United States Patent [19]
Schulz

[11] Patent Number: 6,024,728
[45] Date of Patent: Feb. 15, 2000

[54] VETERINARY SYRINGE WITH DOSING DEVICE

[75] Inventor: Dieter Schulz, Muelheim, Germany

[73] Assignee: Henke-Sass, Wolf GmbH, Tuttlingen, Germany

[21] Appl. No.: 08/963,102

[22] Filed: Nov. 3, 1997

[30] Foreign Application Priority Data

Jan. 15, 1997 [DE] Germany .......................... 297 00 656

[51] Int. Cl.[7] .................................................. A61M 5/315
[52] U.S. Cl. ........................................... 604/224; 604/234
[58] Field of Search ..................... 604/209, 224, 604/233, 183, 227, 234; 222/309, 79, 401

[56] References Cited

U.S. PATENT DOCUMENTS

| | | | |
|---|---|---|---|
| 3,110,310 | 11/1963 | Cislak | 604/224 X |
| 4,364,388 | 12/1982 | Cech | 604/224 |
| 5,807,340 | 9/1998 | Pokras | 604/209 X |

Primary Examiner—Wynn Wood Coggins
Assistant Examiner—A. T. Nguyen
Attorney, Agent, or Firm—McAulay Nissen Goldberg Kiel & Hand, LLP

[57] ABSTRACT

A veterinary syringe with a dosing device for administering medications in different preselectable amounts, comprises a piston rod which projects into a syringe cylinder by a piston provided at a first end of the piston rod and which is supported at a handle at its other end by an actuating lever which is fastened to the other end so as to be swivelable. The piston rod is supported so as to be displaceable longitudinally in a holder which is rigidly connected with the handle. A dosing device is provided between the holder on one side and the piston rod on the other side. At least two longitudinal grooves are arranged parallel to one another and which have different lengths compared with one another are distributed along the outer circumference of the piston rod. An engagement member is provided which is arranged so as to be rotatable about the piston rod and can be moved into one of the grooves.

11 Claims, 2 Drawing Sheets

VETERINARY SYRINGE WITH DOSING DEVICE

BACKGROUND OF THE INVENTION a) Field of the Invention

The invention is directed to a veterinary syringe with a dosing device for administering medications in different preselectable amounts. This veterinary syringe substantially comprises a piston rod which projects into a syringe cylinder by a piston provided at the first end of the piston rod and which is supported at a handle by its other end by means of an actuating lever which is fastened to the other end so as to be swivelable. The piston rod is supported so as to be displaceable longitudinally in a holder which is rigidly connected with the handle. The dosing device is provided between the holder on one side and the piston rod on the other side.

b) Description of the Related Art

In known veterinary syringes with preselectable dosing for administering different amounts of medication, there is an actuating lever for dispensing the medication from the syringe cylinder. The actuating lever is connected with the piston rod in an articulated manner on one side and is fastened to a handle via a joint on the other side so as to be swivelable, this handle being rigidly connected with the holder of the veterinary syringe. The relative motion between the piston rod and syringe cylinder is achieved in that the actuating lever is swiveled against the handle by force applied by hand and the piston is accordingly pressed into the syringe cylinder. In so doing, the force of a spring element must also be overcome; when the force exerted by the hand is reduced, this spring element brings the actuating lever back into the starting position and accordingly brings the piston rod and the piston back into the end position. A dose amount is preselected by means of a slide which is fastened to the holder and is movable vertically to the axis of the piston rod, wherein three catch positions are possible: one catch position on each side of the center of the piston rod, and a middle position.

While the slide allows the piston rod free passage in the middle position, so that the entire amount of medication located in the syringe cylinder can be ejected, the free path of the piston rod is limited in the side catch positions in that a stop which is arranged at the slide and has a protuberance or a recess (depending on construction design) engages at the piston rod and prevents the piston rod from sliding in farther.

Three different dose amounts can be preselected with this veterinary syringe. However, it is disadvantageous that the number of catch positions (left, middle, right), and thus also the dosing amounts that can be preselected, is thereby exhausted. Further, a relatively large expenditure of force in a direction transverse to the handle and to the actuating lever is required to switch from one dosing amount to another, so that the handling of the preselecting mechanism is unfavorable in ergonomic respects. Moreover, this type of slide construction is soiled very easily so that switching becomes increasingly difficult.

OBJECT AND SUMMARY OF THE INVENTION

On this basis, the primary object of the invention is to further develop a veterinary syringe of the generic type described above in such a way that, while retaining the advantage of preselectable dose amounts, the overall construction of the veterinary syringe is further simplified and its handling is considerably facilitated, especially with respect to switching from one dose amount to another.

According to the invention, this object is met in a veterinary syringe of the type mentioned above in that at least two longitudinal grooves which are arranged parallel to one another and which have different lengths compared with one another are distributed along the outer circumference of the piston rod, and in that there is provided an engagement member which is arranged so as to be rotatable about the piston rod and can be moved into one of the grooves.

The arrangement according to the invention substantially simplifies handling of the veterinary syringe when selecting a dosage of medication or when switching from one adjusted dosage of medication to another. Since every groove at the circumference of the piston rod corresponds to a preselectable amount of medication, the engagement member need only be engaged with the groove whose length is adjusted to the desired amount of medication. The selection of the dose amount to be provided is completed simply by moving the engagement member into the corresponding groove. When the piston rod with the piston is moved into the syringe cylinder by means of the actuating lever, this movement process can be carried out until the end of the groove encounters the engagement member. Thus, when the engagement member engages with a groove of short length, the piston can only travel a correspondingly short path in the syringe cylinder and a small dose of medication is injected. But when the engagement member is engaged in a groove of greater length, a large dose of medication is dispensed. In this simple manner, the engagement member reliably limits the depth to which the piston rod penetrates into the syringe cylinder and the advance of the piston and thus ensures that different amounts of medication are preselected. Reproducibility is provided in that the engagement member is secured against axial displacement with respect to the holder, because in this way the movement of the piston rod into and out of the syringe cylinder is always limited to the same position, i.e., at the engagement element.

In an advantageous construction of the invention, the engagement member is held radially in an adjustment ring which is rotatable about the piston rod. It is accordingly possible to move the engagement member easily and quickly by a movement of the finger beyond the grooves at the circumference of the piston rod and, finally, to position it over the groove that corresponds to the dose amount to be selected.

In a preferred construction, the adjustment ring is supported between the piston rod and holder, so that it is possible to guide the adjustment ring exactly and smoothly and the manual positioning of the engagement member over each of the available grooves can be reproduced with a high degree of reliability. Accordingly, it is possible for the veterinarian to handle the syringe in an advantageous manner with respect to ergonomics, because in order to preselect another dose amount it is now no longer necessary to release the veterinary syringe from the hand or to move it into a certain holding position beforehand.

In another construction, the engagement member is fixed with respect to axial displacement relative to the holder. This provides the advantage that the position of the engagement member relative to the ends of the grooves is unequivocally determined in this way and the different dose amounts can therefore be reproduced with great accuracy.

The engagement member is preferably constructed as a screw which is arranged in a bore hole provided radially at the adjustment ring. This enables a simple, economical manufacture of the adjustment ring with the engagement member, since the engagement member can be selected from available standard parts.

In another advantageous construction of the invention, in the initial position of the piston, the end of the engagement member facing the piston rod engages in an annular groove which is provided at least partially in the piston rod, the longitudinal grooves proceeding from this annular groove. This enables a rotation of the adjustment ring around the center of the piston rod in both circumferential directions. Owing to the annular groove extending around the entire circumference of the piston rod, the shortest path can always be selected for positioning the engagement member above any one of the longitudinal grooves.

It is further advantageous when the engagement member is held in the adjustment ring so as to be movable and is pretensioned in a springing manner against the piston rod. This reduces manufacturing costs, especially for the piston rod, since the above-mentioned annular groove is no longer required. When the adjustment ring is rotated in one of the two circumferential directions, the end of the engagement member is pushed over the edge of the groove so that the engagement member is lifted out of the groove with which it was just engaged and, after further rotation of the adjustment ring, locks in the next groove due to the spring pretensioning. If this groove does not correspond to the desired dose amount, the adjustment ring can be further rotated just as easily until the engagement member engages with the groove corresponding to the desired dose amount. In this case, the engagement member is advantageously beveled or rounded conically at its end facing the piston rod, so as to ensure an easy manual rotation of the adjustment ring accompanied by a distinctly perceptible catching of the engagement member in the grooves.

A preferred further development of the invention consists in that marking is provided at the holder and the adjustment ring is provided with a plurality of different markings, each of which indicates a dose amount, wherein the marking at the holder is always located opposite to a marking at the adjustment ring when the engagement member is aligned with one of the grooves. The different markings at the adjustment ring which can comprise numbers or raised portions of different shape symbolize the adjustable dose amounts. This results in the advantage that the adjusted dose amount can be read and monitored, which further simplifies handling of the veterinary syringe.

A further development of the invention consists in that a detent arrangement or catch mechanism is provided between the radial surfaces of the adjustment ring and holder that slide along one another, this catch mechanism being locked in when the engagement member is aligned with one of the grooves. The preselected dose can be changed accurately without looking due to this perceptible snapping in or locking in of the catch mechanism. That is, it is not necessary to ascertain visually that the stationary marking at the syringe body matches the corresponding amount symbol at the adjustment ring. This is especially true when raised portions which can be read by touch by the user and have different shapes corresponding to the individual dose amounts are provided as markings on the adjustment ring.

The catch mechanism advantageously comprises a ball which is incorporated in the holder and pretensioned against the radial surface of the adjustment ring by means of a spring and a recess corresponding to this ball which is provided in the adjustment ring. This represents a simple construction design and accordingly enables a reduction of manufacturing costs.

An embodiment example is explained more fully in the following with the aid of the drawings.

DESCRIPTION OF THE PREFERRED EMBODIMENTS

Figure 1:
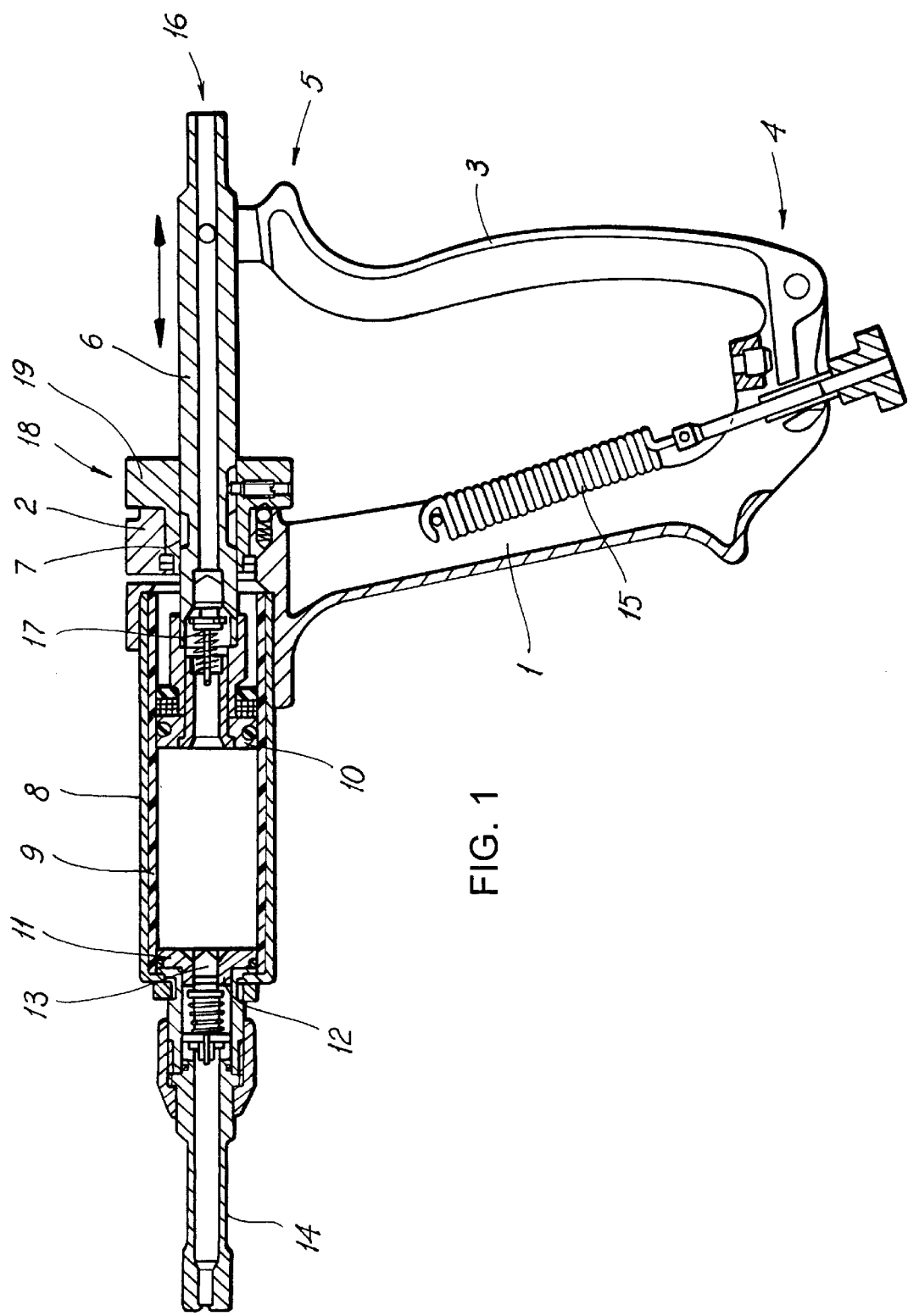
FIG. 1 shows a section through a veterinary syringe constructed as an injection gun with the dosing device according to the invention.

FIG. 1 shows a veterinary syringe constructed as an injection gun with a handle 1, a holder 2 constructed integral with this handle 1, and an actuating lever 3 which is swivelably mounted thereat by its first end 4, the second end 5 of the actuating lever 3 being fastened to a piston rod 6 so as to be swivelable. The piston rod 6 is guided in the holder 2 in a bore hole 7 and projects by a piston 10 into a syringe cylinder 9 which is inserted in a sleeve 8 fastened to the holder 2.

When the actuating lever 3 is moved toward the handle 1, the piston rod 6, and therefore the piston 10, slide further into the syringe cylinder 9 and accordingly press the medication contained in the syringe cylinder 9 through an opening 13 which is provided in the base 11 of the syringe cylinder 9 and is provided with an outlet valve 12 into an injection attachment 14 fitted thereto.

A spring element 15 is installed between the handle 1 and actuating lever 3; the actuating lever 3 is operated against the action of this spring element 15 and is returned to its initial position by the spring element 15 after the injection has been completed. In so doing, the hollow piston rod 6 is guided out of the syringe cylinder 9 again, the outlet valve 12 closes, and the medication is refilled through the hollow piston rod 6 owing to the vacuum in the syringe cylinder 9 to fill the syringe cylinder 9 again. For this purpose, a tube, not shown in the drawings, is provided at the open end 16 of the piston rod 6 and connected with a medication supply vessel which is also not shown. An inlet valve 17 is provided in the piston 10 and closes as soon as the piston 10 or piston rod 6 is moved into the syringe cylinder 9 by the actuating lever 3.

In order to enable the veterinarian to administer different, but exactly dosed, amounts of medication, the depth to which the piston 10 penetrates into the syringe cylinder 9 can be adjusted. A dosing device 18, shown in an enlarged view in FIG. 2, is provided for this purpose.

First, this dosing device comprises an adjustment ring 19 which is mounted so as to be rotatable around the piston rod 6; an engagement member 20 which is constructed in this instance as a threaded pin, for example, is held radially in the adjustment ring 19. The adjustment ring 19 is provided with a bushing-like shoulder 21 which is directed axially to the syringe cylinder 9 and is rotatably mounted between the piston rod 6 and the holder 2. The adjustment ring 19 is secured against axial displacement by a spring ring 22.

The end 23 of the engagement member 20 facing the piston rod surface is narrowed conically and is engaged with a longitudinal groove 24 which is worked into the piston rod 6. Further, an annular groove 25 is provided at the piston rod 6 so as to extend around the full circumference thereof. Proceeding from this annular groove 25 and extending in the direction of the opening 16 of the piston rod 6 there are, in addition to the longitudinal groove 24, also additional longitudinal grooves 24' which are arranged at a distance from the longitudinal groove 24, each of these longitudinal grooves 24' having different lengths compared with the length of groove 24 and accordingly representing different dose amounts.

Figure 2:
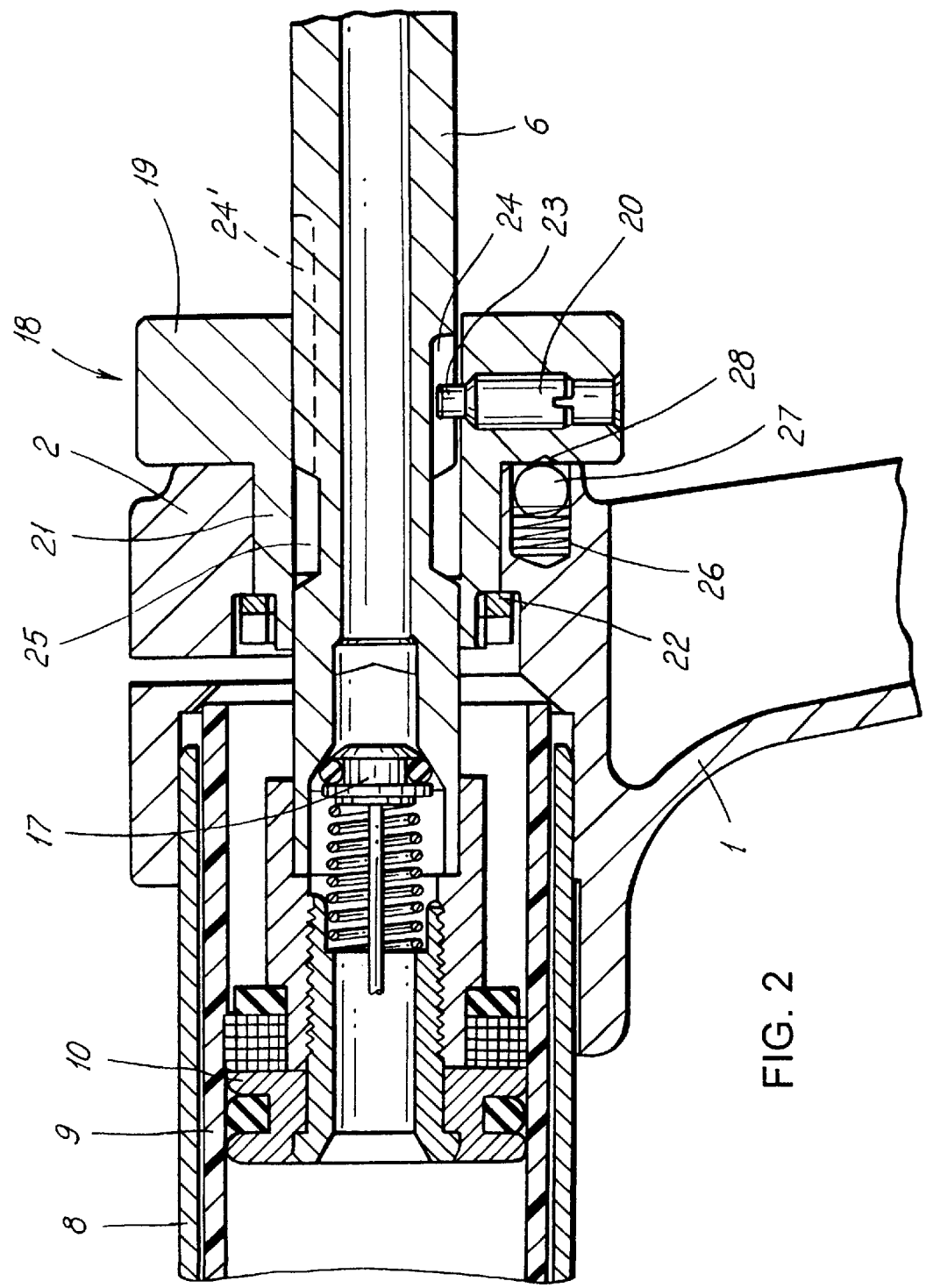
FIG. 2 shows an enlarged partial section in the region of the dosing device of the veterinary syringe.

The position of the piston 10 shown in FIG. 2 corresponds to a position between its two end positions, that is, after a determined amount of the medication contained in the syringe cylinder 9 has been injected. The engagement member 20 projects by its end 23 into the groove 24 which has a determined length. In this view, the injection process has not yet been concluded, since the engagement member 20 still does not contact the end of the groove 24. When the piston 10 moves back into the end position after the adjusted dosage of medication has been completely sprayed out, the end 23 of the engagement member 20 engages in the groove 25. If a different dose amount is to be preselected for the next injection process, the adjustment ring 19 along with the engagement member 20 which is now engaged with the annular groove 25 can be rotated about the piston rod 6 until reaching the groove 24' which corresponds to the desired dose amount.

In order to show that the desired position of the adjustment ring 19 has been reached, a ball 27 which is provided as a catch mechanism between the radial surfaces of the adjustment ring 19 and the holder 2, which radial surfaces slide upon one another, is pretensioned against the radial surface of the adjustment ring 19 by a spring 26 and catches in one of the recesses 28 at the adjustment ring 19 that are assigned to the longitudinal grooves 24. The respective dose setting is signaled when the ball 27 snaps into the recesses 28 of the adjustment ring 19. Further, the adjusted dose amount or, when stamped in numbers are used, the exact value of the adjusted dose amount can be read off from markings (not shown in the drawing) located at the holder 2 and on the adjustment ring 19.

While the foregoing description and drawings represent the preferred embodiments of the present invention, it will be obvious to those skilled in the art that various changes and modifications may be made therein without departing from the true spirit and scope of the present invention.

What is claimed is:

1. A veterinary syringe with a dosing device for administering medications in different preselectable amounts, said veterinary syringe substantially comprising:

a handle and an actuating lever;

a syringe cylinder;

a piston rod which projects into said syringe cylinder;

a piston being provided at a first end of said piston rod and which is supported at the handle at its other end by the actuating lever which is fastened to said other end so as to be swivelable;

a holder for supporting said piston rod, said holder and piston rod being displaceable longitudinally relative to each other, said holder being rigidly connected with said handle;

a dosing device being provided between said holder on one side and said piston rod on the other side;

said piston rod having at least two longitudinal grooves arranged parallel to one another and having different lengths compared with one another, said longitudinal grooves being distributed along the outer circumference of the piston rod, said different lengths corresponding to the different preselected amounts; and an engagement member being provided which is arranged so as to be rotatable about said piston rod and can be moved into one of the grooves.

2. The veterinary syringe according to claim 1, wherein said engagement member is held radially in an adjustment ring which is rotatable about the piston rod.

3. The veterinary syringe according to claim 2, wherein said adjustment ring is supported between said piston rod and holder.

4. The veterinary syringe according to claim 3, wherein said engagement member is fixed with respect to axial displacement relative to the holder.

5. The veterinary syringe according to claim 4, wherein said engagement member is constructed as a screw which is arranged in a bore hole provided radially at the adjustment ring.

6. The veterinary syringe according to claim 1, wherein, in an initial position of the piston, an end of said engagement member facing the piston rod engages in an annular groove which is provided at least partially in the piston rod, the longitudinal grooves emanating from this annular groove.

7. The veterinary syringe according to claim 2, wherein said engagement member is held in the adjustment ring so as to be movable and is pretensioned in a springing manner against the piston rod.

8. The veterinary syringe according to claim 7, wherein the engagement member is beveled or rounded conically at its end facing the piston rod.

9. The veterinary syringe according to claim 1, wherein marking is provided at the holder and said adjustment ring is provided with a plurality of different markings, each of which indicates a dose amount, wherein the mark at the holder is always located opposite to a mark at the adjustment ring when the engagement member is aligned with one of the grooves.

10. The veterinary syringe according to claim 3, wherein a catch mechanism is provided between the radial surfaces of the adjustment ring and holder, which radial surfaces slide along one another, this catch mechanism being locked in when the engagement member is aligned with one of the grooves.

11. The veterinary syringe according to claim 10, wherein the catch mechanism comprises a ball which is incorporated in the holder and pretensioned against the radial surface of the adjustment ring by a spring and a recess corresponding to this ball which is provided in the adjustment ring.

* * * * *